United States Patent [19]
Wang et al.

[11] Patent Number: 5,657,429
[45] Date of Patent: Aug. 12, 1997

[54] AUTOMATED ENDOSCOPE SYSTEM OPTIMAL POSITIONING

[75] Inventors: Yulun Wang, Goleta; Keith Phillip Laby, Santa Barbara, both of Calif.

[73] Assignee: Computer Motion, Inc., Goleta, Calif.

[21] Appl. No.: 481,926

[22] Filed: Jun. 6, 1995

Related U.S. Application Data

[63] Continuation of Ser. No. 167,704, Dec. 15, 1993, abandoned, which is a continuation-in-part of Ser. No. 72,982, Jun. 3, 1993, Pat. No. 5,524,180, which is a continuation-in-part of Ser. No. 5,604, Jan. 19, 1993, abandoned, which is a continuation-in-part of Ser. No. 927,801, Aug. 10, 1992, abandoned.

[51] Int. Cl.$^6$ .............................. A61B 1/00; A61C 19/04; G06F 15/00
[52] U.S. Cl. .................. 395/86; 395/92; 395/80; 395/94; 901/12; 901/31; 901/41; 901/47; 606/19; 606/46; 600/118
[58] Field of Search .................... 395/86, 80, 92, 395/94; 901/12, 31, 41, 47; 364/413.02, 413.13; 128/4; 606/19, 46

[56] References Cited

U.S. PATENT DOCUMENTS

| | | | |
|---|---|---|---|
| 4,221,997 | 9/1980 | Flemming | 318/574 |
| 4,456,961 | 6/1984 | Price et al. | 318/568 |
| 4,474,174 | 10/1984 | Petruzzi | 128/4 |
| 4,517,963 | 5/1985 | Michel | 128/6 |
| 4,655,257 | 4/1987 | Iwashita | 128/4 |
| 4,676,243 | 6/1987 | Clayman | 128/305 |
| 4,728,974 | 3/1988 | Nio et al. | 901/44 |
| 4,791,934 | 12/1988 | Brunnett | 128/653 |
| 4,794,912 | 1/1989 | Lia | 128/4 |
| 4,815,006 | 3/1989 | Anderson et al. | 318/568 |
| 4,854,301 | 8/1989 | Nakajima | 128/4 |
| 4,863,133 | 9/1989 | Bonnell | 248/278 |
| 4,930,494 | 6/1990 | Takehana et al. | 128/4 |
| 4,979,933 | 12/1990 | Runge | 495/215 |
| 4,979,949 | 12/1990 | Matsen, III et al. | 606/53 |
| 4,996,975 | 3/1991 | Nakamura | 128/4 |
| 5,020,001 | 5/1991 | Yamamoto et al. | 364/474.13 |
| 5,065,741 | 11/1991 | Uchiyama et al. | 128/24 EL |
| 5,078,140 | 1/1992 | Kwoh | 901/6 |
| 5,086,401 | 2/1992 | Glassman et al. | 395/94 |
| 5,142,930 | 9/1992 | Allen et al. | 901/47 |
| 5,145,227 | 9/1992 | Monford, Jr. | 901/40 |
| 5,184,601 | 2/1993 | Putman | 128/4 |
| 5,201,325 | 4/1993 | McEwen et al. | 128/20 |
| 5,201,743 | 4/1993 | Haber et al. | 606/147 |
| 5,217,003 | 6/1993 | Wilk | 128/4 |

(List continued on next page.)

FOREIGN PATENT DOCUMENTS

| | | |
|---|---|---|
| 0239409 | 9/1987 | European Pat. Off. . |
| 9204118 U | 7/1992 | Germany . |
| WO91/04711 | 4/1991 | WIPO . |

OTHER PUBLICATIONS

Fu, et al, "Robotics: Control, Sensing, Vision and Intelligence", McGraw-Hill Book Company; 1987.

*Primary Examiner*—George B. Davis
*Attorney, Agent, or Firm*—Blakely Sokoloff Taylor & Zafman

[57] ABSTRACT

A robotic system that moves a surgical instrument in response to the actuation of a control panel that can be operated by a surgeon. The robotic system has an end effector that is adapted to hold a surgical instrument such as an endoscope. The end effector is coupled to a robotic arm assembly which can move the endoscope relative to a patient. The system includes a computer which controls the movement of a robotic arm in response to input signals received from the control panel. The robotic system is mounted to a cart which can be wheeled to and from an operating table. The cart has a clamping mechanism which attaches the cart to the table. The system also contains a spring loaded mount plate that allows the robotic arm to be rotated and adjusted relative to the cart and the patient. Both the robotic arm and the control panel are encapsulated by protective bags that prevent the system from being contaminated.

7 Claims, 14 Drawing Sheets

OTHER PUBLICATIONS

| | | | |
|---|---|---|---|
| 5,221,283 | 6/1993 | Chang | 606/130 |
| 5,228,429 | 7/1993 | Hatano | 128/4 |
| 5,230,623 | 7/1993 | Guthrie et al. | 433/72 |
| 5,236,432 | 8/1993 | Matsen, III et al. | 606/88 |
| 5,251,127 | 10/1993 | Raab | 364/413.13 |
| 5,271,384 | 12/1993 | McEwen et al. | 901/41 |
| 5,279,309 | 1/1994 | Taylor et al. | 128/782 |
| 5,305,203 | 4/1994 | Raab | 364/413.13 |
| 5,343,391 | 8/1994 | Mushabac | 364/413.28 |

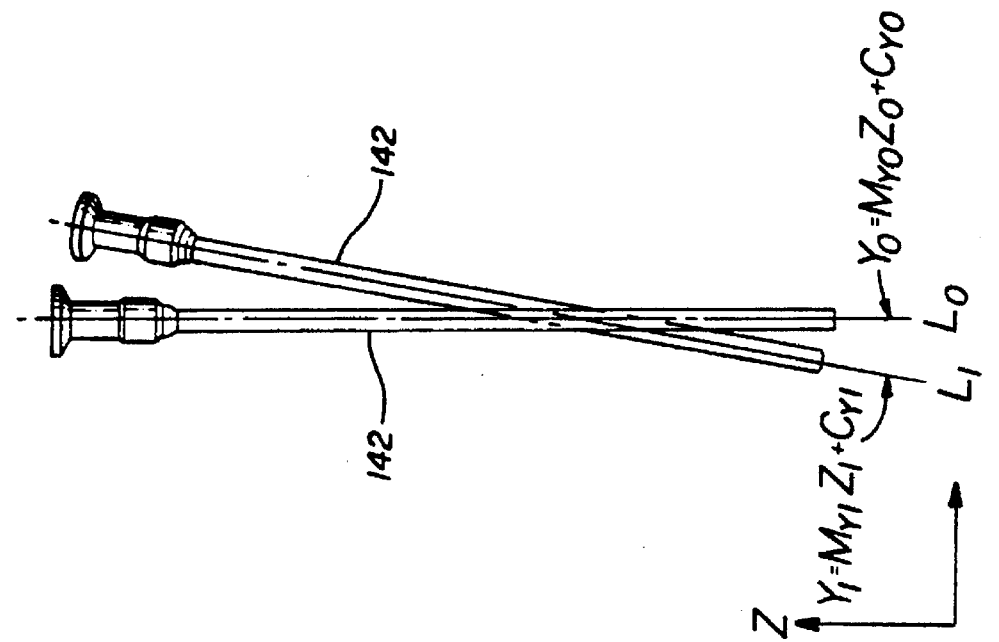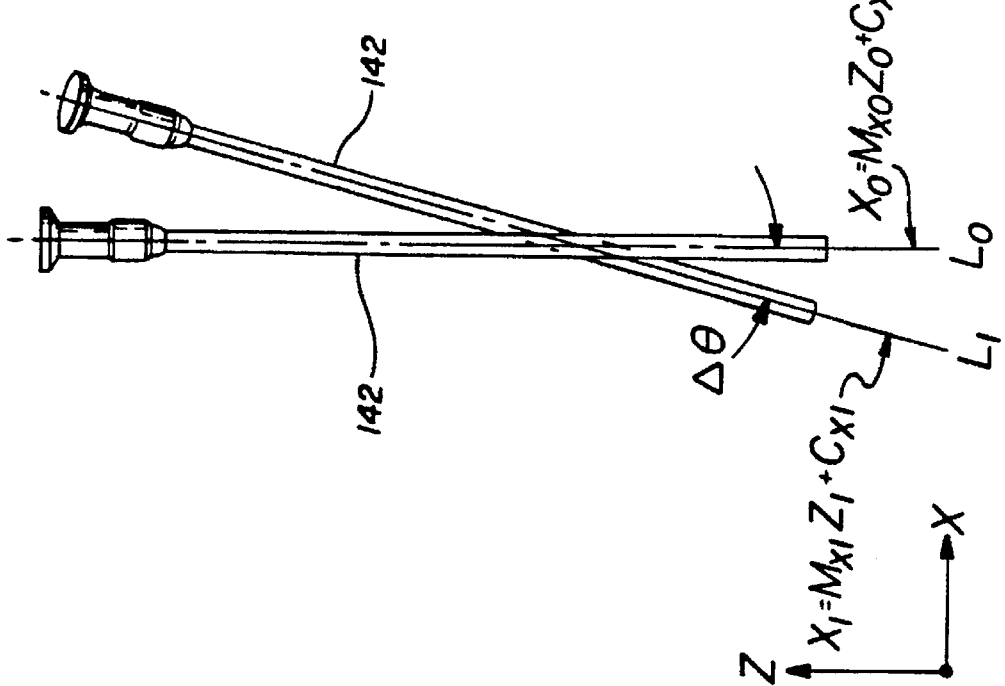
FIG. 16

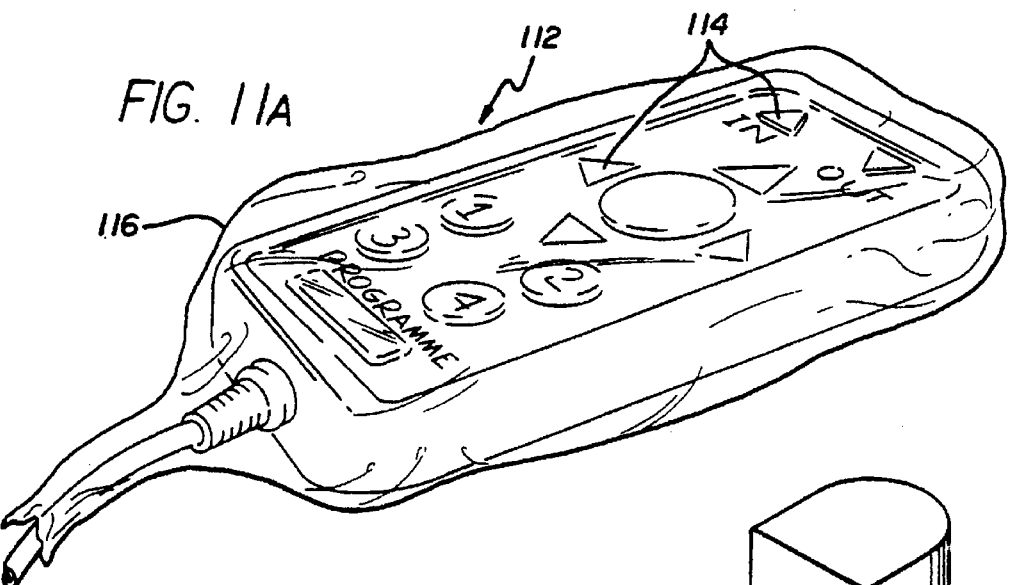
FIG. 11A
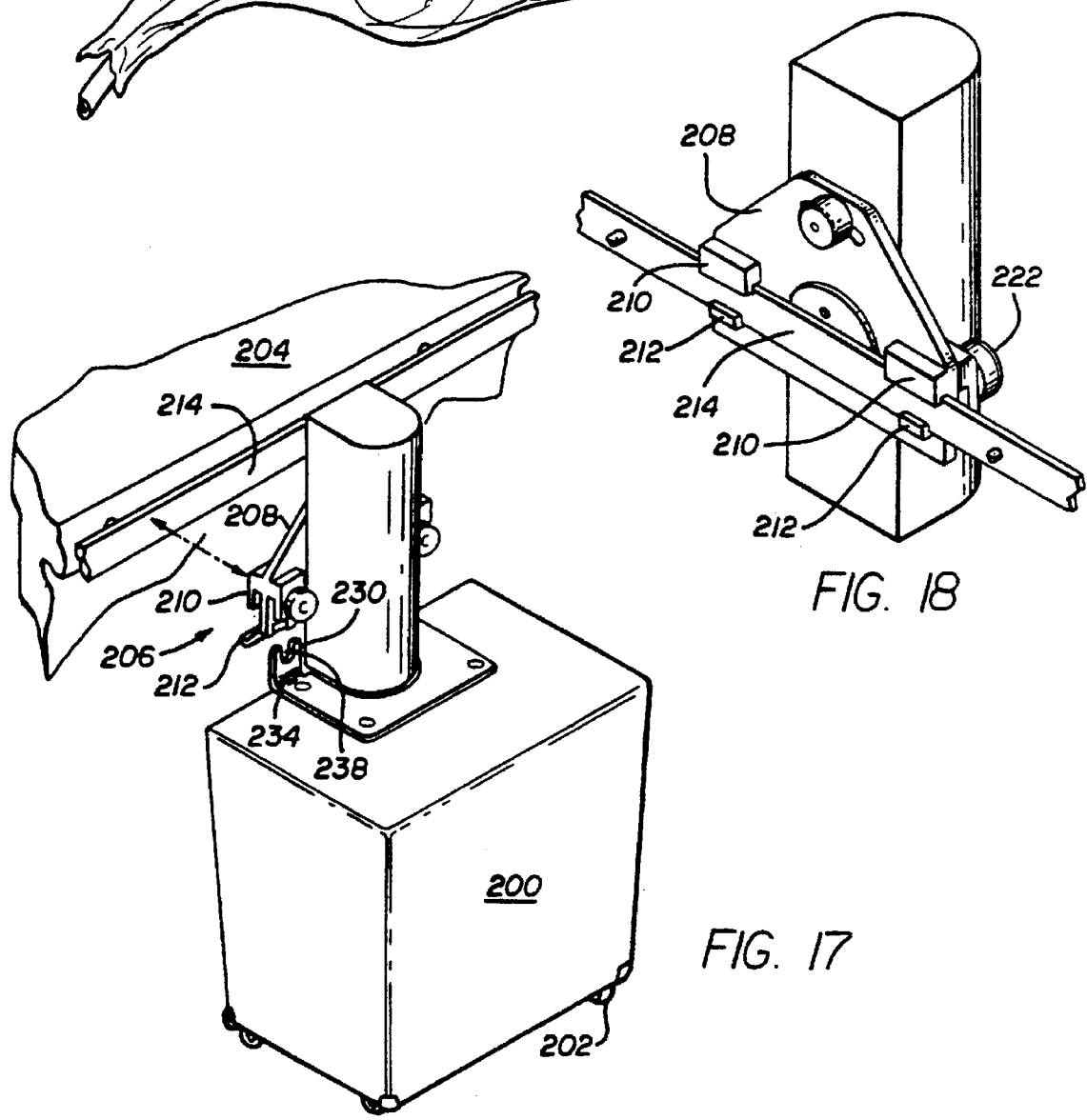
FIG. 18
FIG. 17

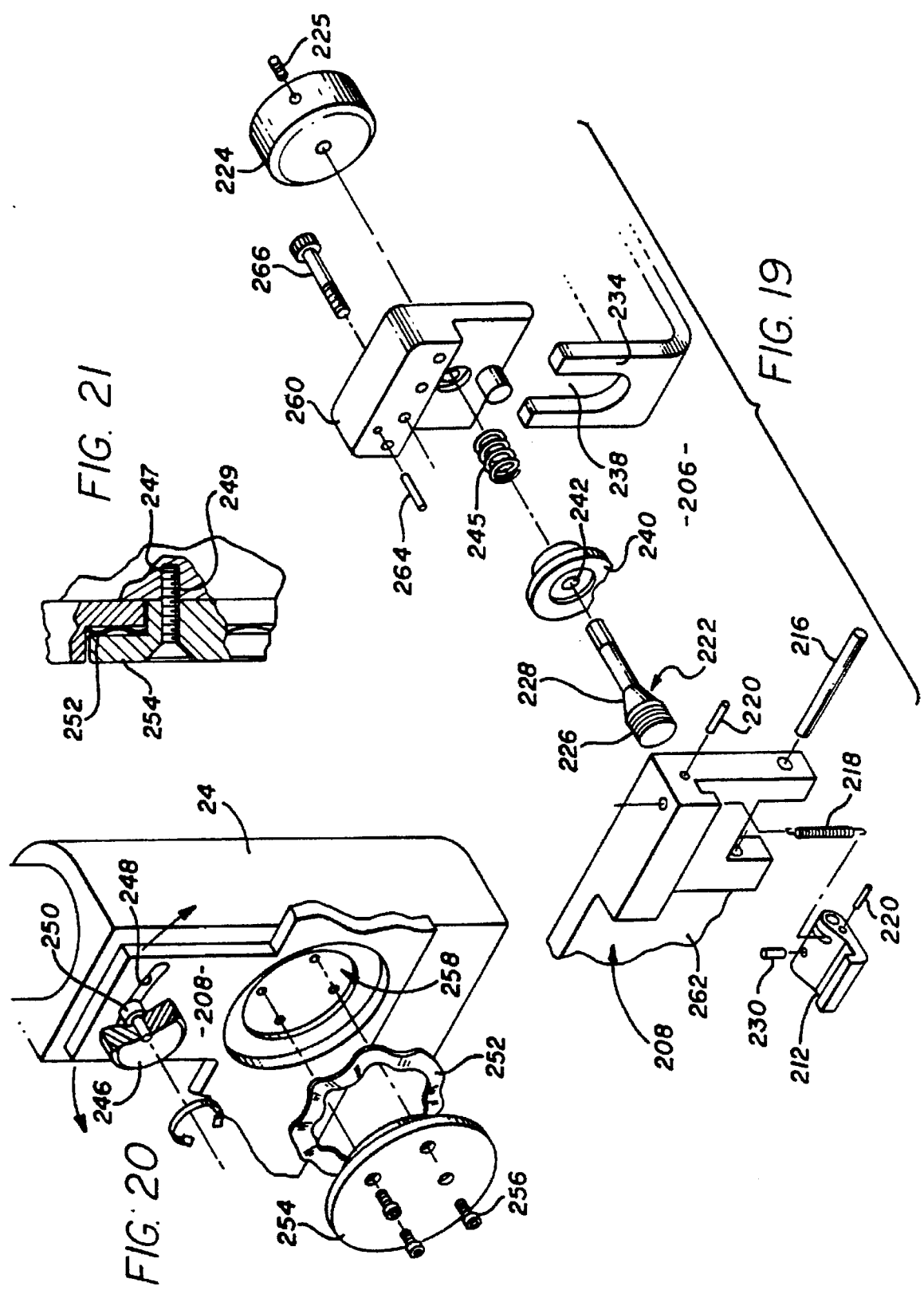

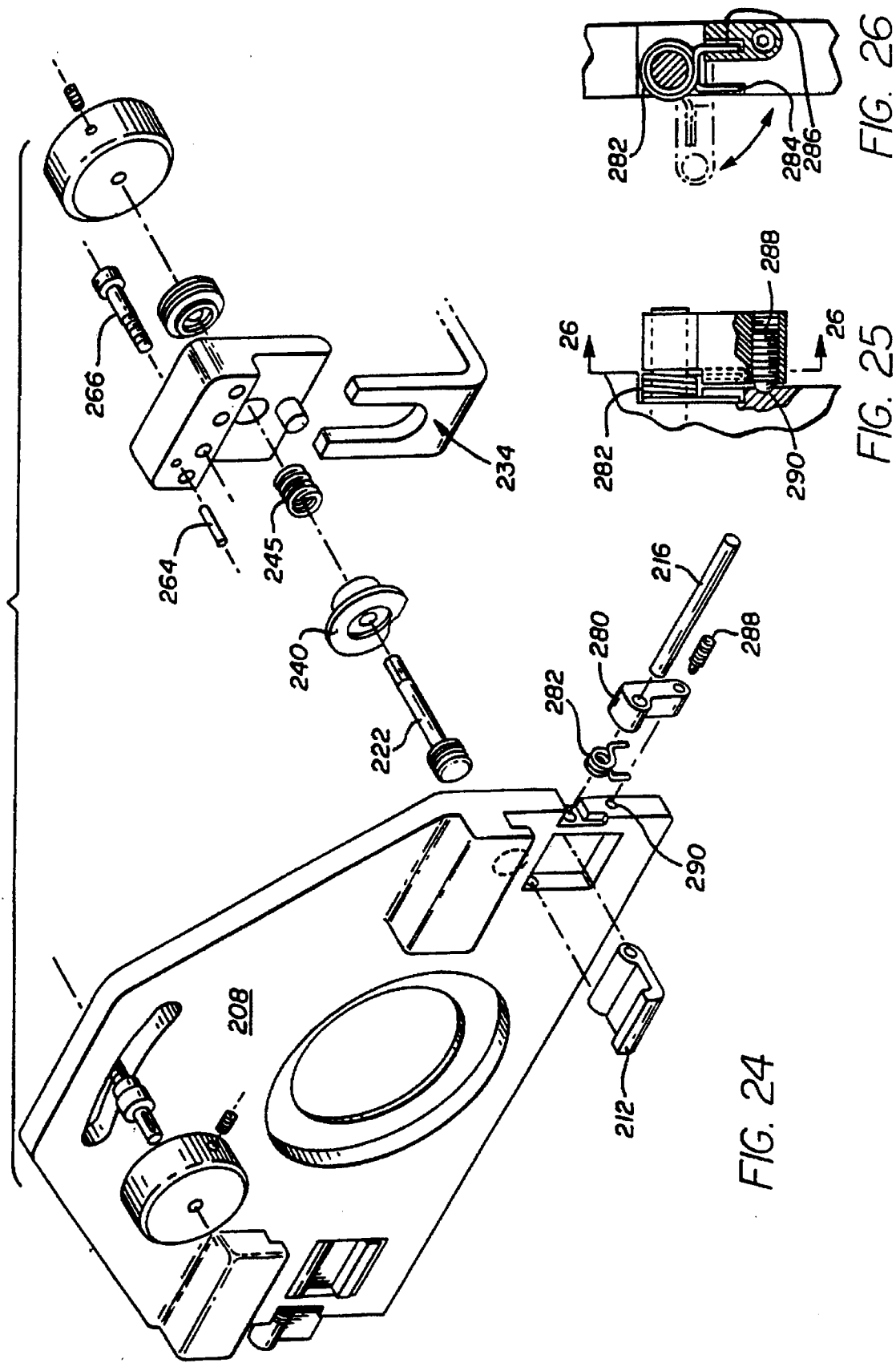

5,657,429

AUTOMATED ENDOSCOPE SYSTEM OPTIMAL POSITIONING

This application is a continuation of application Ser. No. 08/167,704 filed on Dec. 15, 1993, now abandoned; which is a continuation-in-part of application Ser. No. 08/072,982 filed on Jun. 3, 1993, U.S. Pat. No. 5,524,180; which is a continuation-in-part of application Ser. No. 08/005,604 filed on Jan. 19, 1993, now abandoned; which is a continuation-in-part of application Ser. No. 07/927,801 filed on Aug. 10, 1992, now abandoned.

BACKGROUND OF THE INVENTION

1. Field of the Invention

The present invention relates to a robotic system for remotely controlling the position of a surgical instrument.

2. Description of Related Art

Endoscopes typically contain a lens that is coupled to a visual display by a fiber optic cable. Such a system allows the user to remotely view an image in front of the scope. Endoscopes are commonly used in a surgical procedure known as laparoscopy, which involves inserting the endoscope into the patient through a small incision in the abdomen. The endoscope allows the surgeon to internally view the patient without being in a direct line of sight with the object. The use of an endoscope typically reduces the size of the incision needed to perform a surgical procedure.

Endoscopes are commonly used to assist the surgeon in removing the gall bladder of a patient. Because the surgeon typically requires both hands to remove a gall bladder, the endoscope must be held and operated by a assistant. During the surgical procedure, the surgeon must frequently instruct the assistant to move the endoscope within the patient. Such a method can be time consuming as the surgeon may have to relay a series of instructions until the assistant has positioned the endoscope in the proper location. Additionally, the assistant may be unable to consistently hold the instrument in a fixed position, resulting in a moving image. This is particularly true for surgical procedures that extend over a long period of time.

There is presently a system marketed by Leonard Medical Inc. which mechanically holds an endoscope. The Leonard Medical system is an articulated mechanism which has a plurality of pneumatically powered joints that hold the endoscope in a fixed position. To move the endoscope, the pneumatic powered joints must be initially released into a relaxed condition. The surgeon or assistant then moves the scope and reactivates the pneumatic system. Although the Leonard system holds the endoscope in one position, the system requires the surgeon or assistant to constantly deactivate/activate the pneumatics and manually move the scope. Such a system interrupts the surgery process and increases the time of the surgical procedure. It would be desirable to provide a system that allows the surgeon to directly and efficiently control the movement of an endoscope.

SUMMARY OF THE INVENTION

The present invention is a robotic system that moves a surgical instrument in response to the actuation of a control panel that can be operated by the surgeon. The robotic system has an end effector that is adapted to hold a surgical instrument such as an endoscope. The end effector is coupled to a robotic arm assembly which can move the endoscope relative to the patient. The system includes a computer which controls the movement of the robotic arm in response to input signals from the control panel.

The robotic system is mounted to a cart which can be wheeled to and from an operating table. The cart has a clamping mechanism which attaches the cart to the table. The system also contains a spring loaded mount plate that allows the robotic arm to be rotated and adjusted relative to the cart and the patient. Both the robotic arm and the control panel are encapsulated by protective bags that prevent the system from being contaminated. The bags are removable and allow the system to be reused without having to scrub and decontaminant the arm or control panel.

BRIEF DESCRIPTION OF THE DRAWINGS

The objects and advantages of the present invention will become more readily apparent to those ordinarily skilled in the art after reviewing the following detailed description and accompanying drawings, wherein:

FIG. 11a is a top view of a protective sterile bag which encapsulates a hand held control pad of the robotic arm assembly;

FIG. 16 is a schematic of the surgical instrument being moved relative to a pivot point;

FIG. 17 is a perspective view showing the robotic arm assembly mounted to a cart and a mounting assembly;

FIG. 18 is a front perspective view showing the robotic arm assembly mounted to the mounting assembly;

FIG. 19 is an exploded view of a clamping assembly which clamps the robotic arm assembly to an operating table;

FIG. 20 is a partially exploded view showing the robotic arm assembly coupled to the mounting assembly;

FIG. 21 is a cross-sectional view of the mounting plate attached to the linear actuator of the robotic arm;

FIG. 24 is an exploded view of an alternate embodiment of the clamping mechanism;

FIG. 25 is a cross-sectional view of a detent portion of a handle

FIG. 26 is a cross-sectional view of the handle;

DETAILED DESCRIPTION OF THE INVENTION

Figure 1:
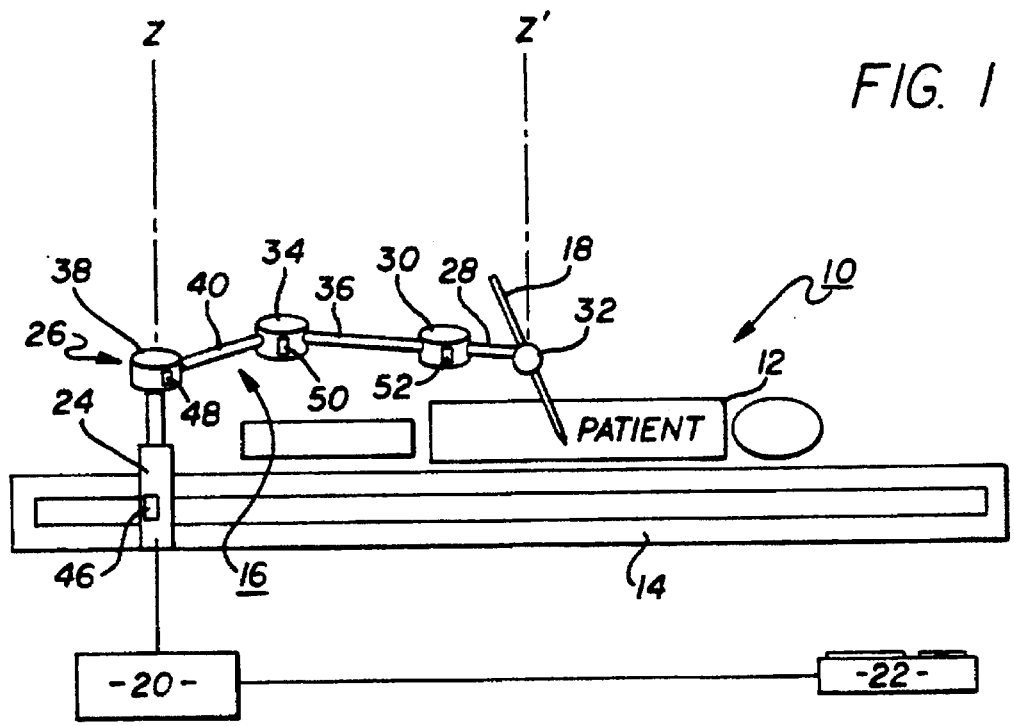
FIG. 1 is a side view of a robotic system of the present invention.
Figure 2:
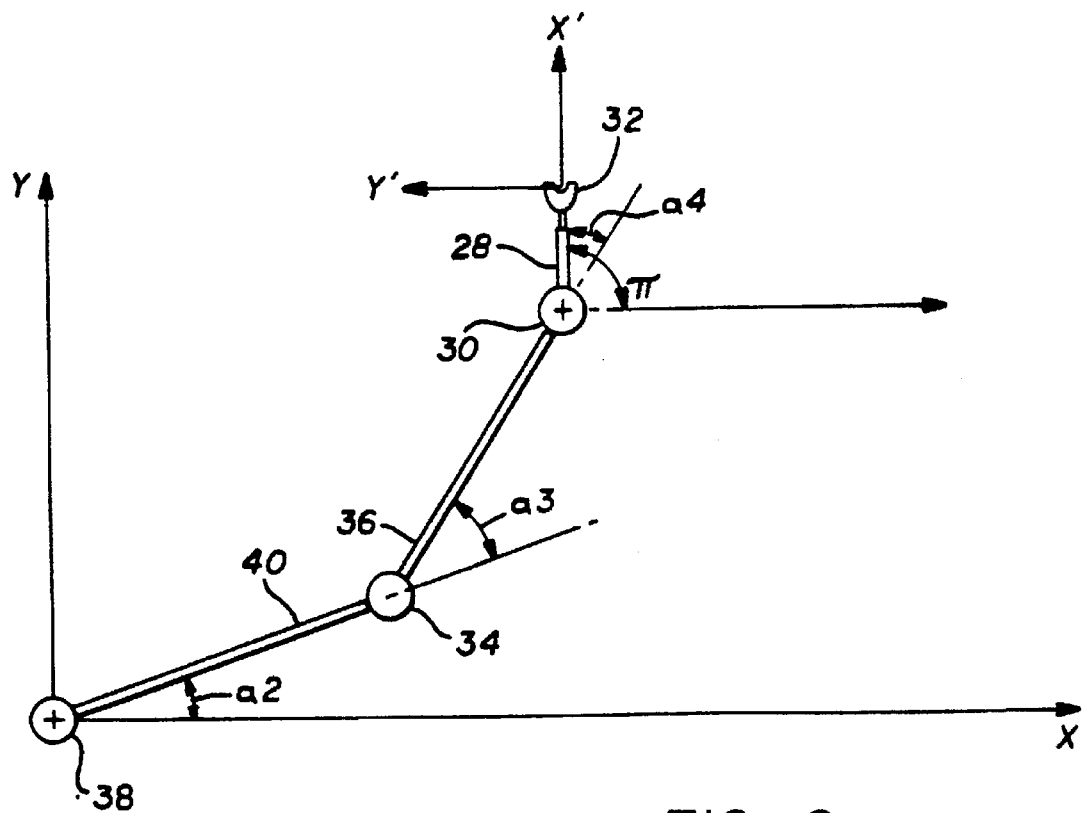
FIG. 2 is a top view of the robotic system of FIG. 1.

Referring to the drawings more particularly by reference numbers, FIGS. 1 and 2 show a robotic system 10 of the present invention. The system 10 is typically used in a sterile operating room where a surgeon (not shown) performs a surgical procedure on a patient 12. The patient 12 is placed on a operating table 14. Attached to the table 14 is a robotic arm assembly 16 which can move a surgical instrument 18 relative to the table 14 and the patient 12. The surgical instrument 18 is typically an endoscope which is inserted into the abdomen of the patient 12. The endoscope 18 enters the patient through cannula, wherein the scope 18 rotate about a cannula pivot point. The endoscope is typically connected to a display screen (not shown) which allows the surgeon to view the organs, etc. of the patient. Although an endoscope is described and shown, it is to be understood that the present invention can be used with other surgical instruments.

The system 10 has a computer 20 that is connected to the robotic arm assembly 16 and a foot pedal 22. The foot pedal 22 is located in close proximity to the operating table 14, so that the surgeon can operate the foot pedal 22 while performing a surgical procedure. The system 10 is constructed so that the surgeon can move the surgical instrument 18 by merely depressing the foot pedal 22.

The robotic arm assembly 16 includes a linear actuator 24 fixed to the table 14. The linear actuator 24 is connected to a linkage arm assembly 26 and adapted to move the linkage assembly 26 along the z axis of a first coordinate system. As shown in FIG. 2, the first coordinate system also has an x axis and a y axis. The linear actuator 24 preferably has an electric motor which turns a ball screw that moves the output shaft of the actuator.

The linkage arm assembly 26 includes a first linkage arm 28 attached to a first rotary actuator 30 and an end effector 32. The first rotary actuator 30 is adapted to rotate the first linkage arm 28 and end effector 32 in a plane perpendicular to the z axis (x-y plane). The first rotary actuator 30 is connected to a second rotary actuator 34 by a second linkage arm 36. The second actuator 34 is adapted to rotate the first actuator 30 in the x-y plane. The second rotary actuator 34 is connected to a third rotary actuator 38 by a third linkage arm 40. The third rotary actuator 38 is connected to the output shaft of the linear actuator 24 and adapted to rotate the second rotary actuator 34 in the x-y plane. The rotary actuators are preferably electric motors with output shafts attached to the respective linkage arms. The actuators 30, 34 and 38 preferably have gear reduction boxes to increase the torque at the linkage arms relative to the electric motors. The electric motors of the actuators 24, 30, 34 and 38 rotate in response to output signals provided by the computer 20.

Figure 3:
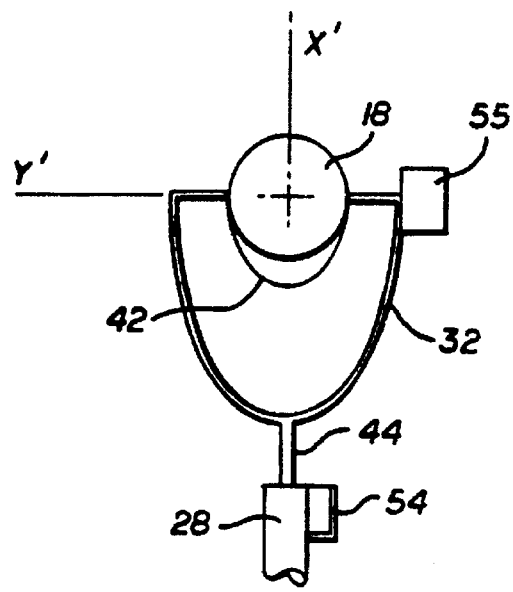
FIG. 3 is a top view of an end effector used to hold an endoscope.

As shown in FIG. 3, the end effector 32 has a clamp 42 which can grasp and hold the endoscope 18. The clamp 42 may be constructed as a wire with a loop that has a diameter smaller than the outside diameter of the scope 18. The clamp 42 allows the scope to be easily attached to and removed from the robotic arm assembly 16. Although a simple wire clamp is shown and described, it is to be understood that the end effector 32 may have any means required to secure the surgical instrument 18. As shown in FIGS. 1 and 2, the junction of the endoscope 18 and the end effector 32 define a second coordinate system which has an x' axis, a y' axis and a z' axis. The junction of the end effector 32 and endoscope 18 also define the origin of a third coordinate system which has a x" axis, a y" axis and a z" axis that is parallel with the longitudinal axis of the endoscope 18.

The end effector 32 has a shaft 44 which can be coupled to the first linkage arm 28. The first linkage arm 28 may have a bearing which allows the end effector 32 to rotate about the longitudinal axis of the arm 28. The end effector 32 may be constructed so that the clamp 42 and scope 18 can rotate about the y' axis. The end effector 32 is preferably constructed to be detached from the first linkage arm 28, so that a sterile instrument can be used for each surgical procedure. The robotic system 10 may also have a bag or cover to encapsulate the robotic arm assembly 16 to keep the assembly 16 sterile.

The actuators 24, 30, 34 and 38 may each have position sensors 46–52 that are connected to the computer 20. The sensors may be potentiometers that can sense the rotational movement of the electric motors and provide feedback signals to the computer 20. The end effector 32 may also have a first joint position sensor 54 that senses the angular displacement of the effector about the x' axis and a second joint position sensor 55 which senses the angular displace of the scope about the y' axis.

Figure 4:
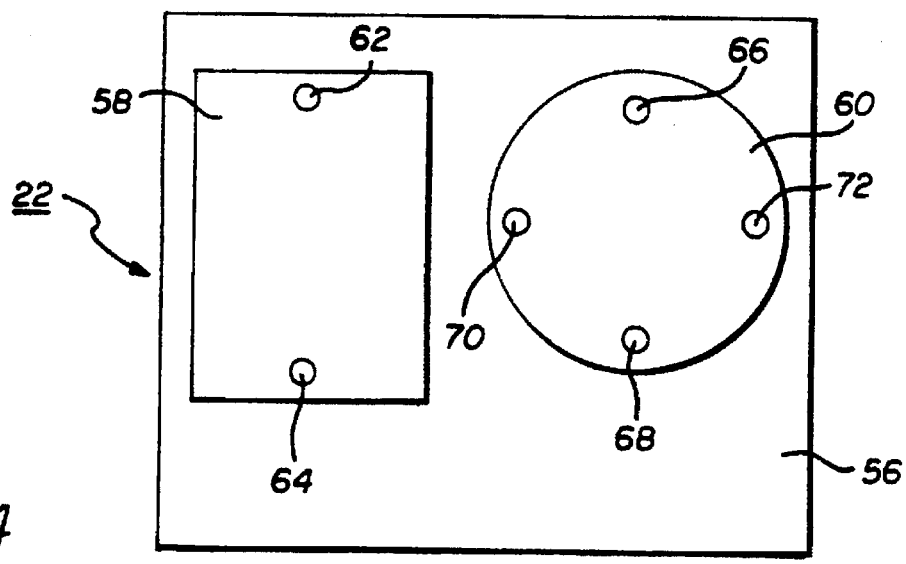
FIG. 4 is a top view of a foot pedal of the system of FIG. 1.
Figure 5:
FIG. 5 is a cross-sectional view of the foot pedal of FIG. 4.

FIGS. 4 and 5 show a preferred embodiment of the foot pedal 22. The foot pedal 22 has a housing 56 that supports a first foot switch 58 and a second foot switch 60. The first foot switch 58 has a first pressure transducer 62 and a second pressure transducer 64. The second foot switch 60 has third 66, fourth 68, fifth 70 and sixth 72 pressure transducers. The transducers are each connected to a corresponding operational amplifier that provides a voltage input to the computer 20. The pressure transducers 62–72 are constructed so that the resistance of each transducer decreases as the surgeon increases the pressure on the foot switches. Such a transducer is sold by interlink Electronics. The decreasing transducer resistance increases the input voltage provided to the computer 20 from the operational amplifier. Each transducer corresponds to a predetermined direction in the third coordinate system. In the preferred embodiment, the first pressure transducer 62 corresponds to moving the endoscope toward the image viewed by the surgeon. The second transducer 64 moves the scope away from the image. The third 66 and fourth 68 transducers move the scope 18 "up" and "down", respectively, and the fifth 70 and sixth 72 transducers move the scope 18 "left" and "right", respectively.

Figure 6:
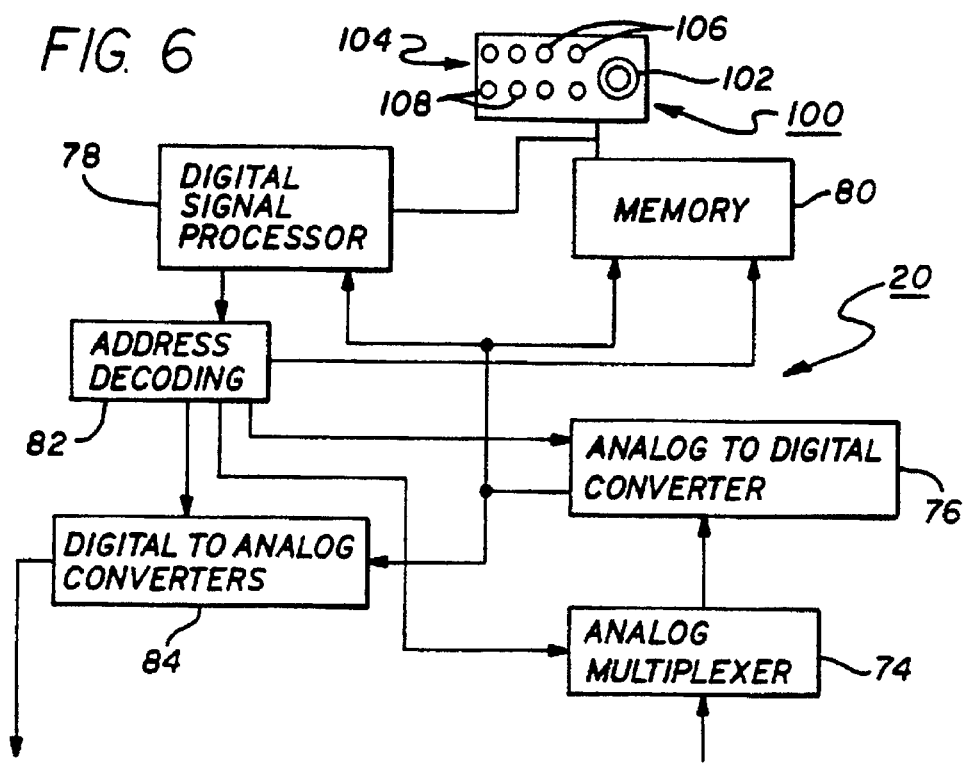
FIG. 6 is a schematic of a computer of the robotic system shown in FIG. 1.

FIG. 6 shows a schematic of the computer 20. The computer 20 has a multiplexer 74 which is connected to the pressure transducers and the position sensors. In the preferred embodiment, the multiplexer 74 has 12 channels, one channel for each sensor and transducer. The multiplexer 74 is connected to a single analog to digital (A/D) converter 76.

The computer also has a processor 78 and memory 80. The A/D converter 76 is constructed so that the converter can provide the processor 78 with a binary string for each voltage level received from the input signals of the system. By way of example, the transducers may provide a voltage ranging between −10 to 10 (V) and the converter 76 may output a different 12 bit binary string for each voltage level. An input signal of 1.0 V may correspond to the binary string 000011001010, 2.0 V may correspond to 000111010100 and so forth and so on.

The processor 78 is connected to an address decoder 82 and four separate digital to analog (D/A) converters 84. Each D/A converter is connected to an actuator 26, 30, 34 or 38. The D/A converters 84 provide analog output signals to the actuators in response to output signals received from the processor 78. The analog output signals preferably have a sufficient voltage level to energize the electric motors and move the robotic arm assembly. The D/A converters 84 may be constructed so that a binary 1 from the processor produces an analog output signal that drives the motors. In such an embodiment, the motors are energized for as long as the processor provides a binary 1 output signal. The decoder 82 correlates the addresses provided by the processor with a corresponding D/A converter, so that the correct motor(s) is driven. The address decoder 82 also provides an address for the input data from the A/D converter so that the data is associated with the correct input channel.

The processor 78 computes the movement of the robotic arm assembly 16 in accordance with the following equations.

$$a3 = \pi - \cos^{-1}\left( \frac{(x - L3\cos(\pi))^2 + (y - L3\sin(\pi))^2 - L1^2 - L2^2}{2L1L2} \right) \quad (1)$$

$$A = \cos^{-1}\left( \frac{(x - L3\cos(\pi))^2 + (y - L3\sin(\pi))^2 + L1^2 - L2^2}{2L1\sqrt{(x - L3\cos(\pi))^2 + (y - L3\sin(\pi))^2}} \right)$$

$$a0 = \tan^{-1}2\left( \frac{y - L3\sin(\pi)}{x - L3\sin(\pi)} \right)$$

$$a2 = a0 +/- A$$

$$a4 = \pi - a2 - a3$$

where;
- a2=angle between the third linkage arm and the x axis.
- a3=angle between the second linkage arm and the longitudinal axis of the third linkage arm.
- a4=angle between the first linkage arm and the longitudinal axis of the second linkage arm.
- L1=length of the third linkage arm.
- L2=length of the second linkage arm.
- L3=length of the first linkage arm.
- Π=the angle between the first linkage arm and the x' axis of the second coordinate system.
- x=coordinate of the end effector in the first coordinate system.
- y=coordinate of the end effector in the first coordinate system.

To move the end effector to a new location of the x-y plane the processor 78 computes the change in angles a2, a3 and a4, and then provides output signals to move the actuators accordingly. The original angular position of the end effector is provided to the processor 78 by the sensors 46–55. The processor moves the linkage arms an angle that corresponds to the difference between the new location and the original location of the end effector. A differential angle Δa2 corresponds to the amount of angular displacement provided by the third actuator 38, a differential angle Δa3 corresponds to the amount of angular displacement provided by the second actuator 34 and a differential angle Δa4 corresponds to the amount of angular displacement provided by the first actuator 30.

To improve the effectiveness of the system 10, the system is constructed so that the movement of the surgical instrument as seen by the surgeon, is always in the same direction as the movement of the foot pedal. Thus when the surgeon presses the foot switch to move the scope up, the scope always appears to move in the up direction. To accomplish this result, the processor 78 converts the desired movement of the end of the endoscope in the third coordinate system to coordinates in the second coordinate system, and then converts the coordinates of the second coordinate system into the coordinates of the first coordinate system.

The desired movement of the endoscope is converted from the third coordinate system to the second coordinate system by using the following transformation matrix;

$$\begin{pmatrix} \Delta x' \\ \Delta y' \\ \Delta z' \end{pmatrix} = \begin{pmatrix} \cos(a6) & 0 & -\sin(a6) \\ -\sin(a5)\sin(a6) & \cos(a5) & -\sin(a5)\cos(a6) \\ \cos(a5)\sin(a6) & \sin(a5) & \cos(a5)\cos(a6) \end{pmatrix} \begin{pmatrix} \Delta x'' \\ \Delta y'' \\ \Delta z'' \end{pmatrix} \quad (2)$$

where
- Δx″=the desired incremental movement of the scope along the x″ axis of the third coordinate system.
- Δy″=the desired incremental movement of the scope along the y″ axis of the third coordinate system.
- Δz″=the desired incremental movement of the scope along the z″ axis of the third coordinate system.
- a5=the angle between the z' axis and the scope in the y'-z' plane.
- a6=the angle between the z' axis and the scope in the x'-z' plane.
- Δx'=the computed incremental movement of the scope along the x' axis of the second coordinate system.
- Δy'=the computed incremental movement of the scope along the y' axis of the second coordinate system.
- Δz'=the computed incremental movement of the scope along the z' axis of the second coordinate system.

Figure 7:
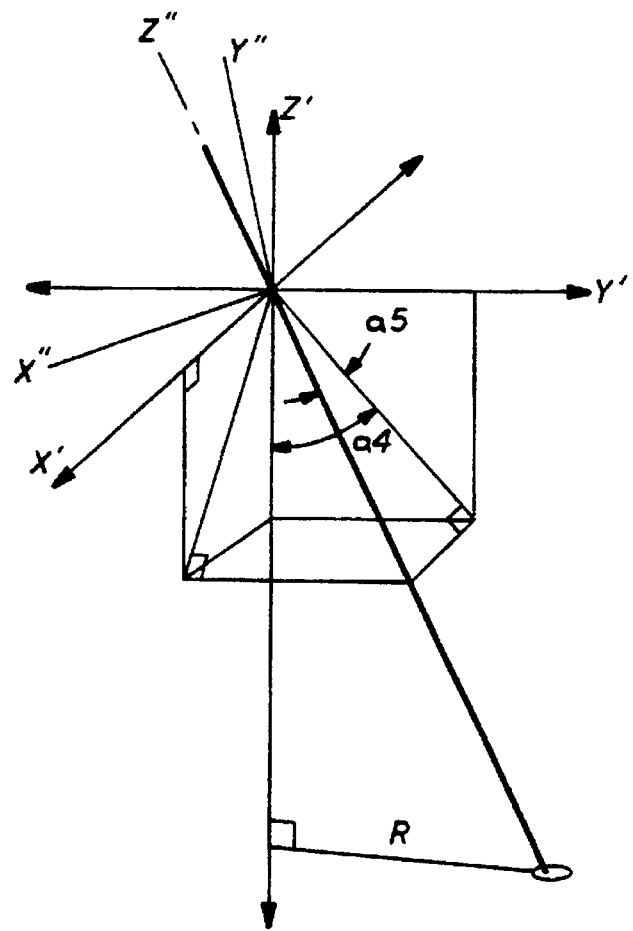
FIG. 7 is a schematic of the endoscope oriented in a second coordinate system.

The angles a5 and a6 are provided by the first 54 and second joint position sensors located on the end effector 32. The angles a5 and a6 are shown in FIG. 7.

The desired movement of the endoscope is converted from the second coordinate system to the first coordinate system by using the following transformation matrix;

$$\begin{pmatrix} \Delta x \\ \Delta y \\ \Delta z \end{pmatrix} = \begin{pmatrix} \cos(\pi) & -\sin(\pi) & 0 \\ \sin(\pi) & \cos(\pi) & 0 \\ 0 & 0 & 1 \end{pmatrix} \begin{pmatrix} \Delta x' \\ \Delta y' \\ \Delta z' \end{pmatrix} \quad (3)$$

where;
- Δx'=the computed incremental movement of the scope along the x' axis of the second coordinate system.
- Δy'=the computed incremental movement of the scope along the y' axis of the second coordinate system.
- Δz'=the computed incremental movement of the scope along the z' axis of the second coordinate system.
- Π=is the angle between the first linkage arm and the x axis of the first coordinate system.
- Δx=the computed incremental movement of the scope along the x axis of the first coordinate system.
- Δy=the computed incremental movement of the scope along the y axis of the first coordinate system.

Δz=the computed incremental movement of the scope along the z axis of the first coordinate system.

The incremental movements Δx and Δy are inserted into the algorithms (1) described above for computing the angular movements (Δa2, Δa3 and Δa4) of the robotic arm assembly to determine the amount of rotation that is to be provided by each electric motor. The value Δz is used to determine the amount of linear movement provided by the linear actuator 26.

After each movement of the endoscope a new Π value must be computed to be used in the next incremental movement of the scope. The scope is typically always in the y'–z' plane, therefore the Π value only changes when the end effector is moved along the y' axis. The new Π angle can be computed with the following equations:

$$d = \left| \frac{m}{\tan(a6)} \right| \quad (4)$$

$$r = |d \sin(a5)|$$

$$\Delta \pi = \tan^{-1} \frac{m}{r}$$

where;
- d=the length of the endoscope between the end effector and the cannula pivot point.
- the distance along the y' axis between the end effector and the cannula pivot point.
- the incremental movement of the scope.

The new Π value is computed and stored in the memory of the computer for further computation.

Figure 8:
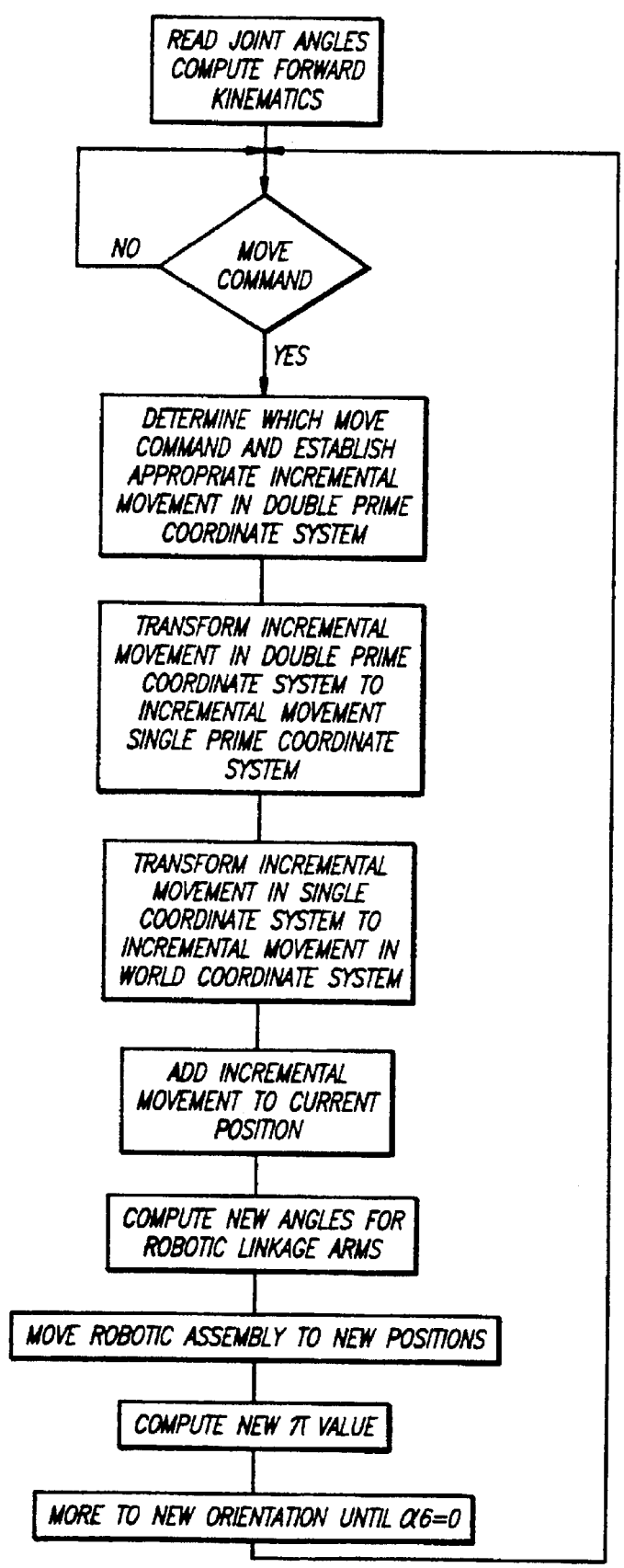
FIG. 8 is a flowchart showing the operation of the system.

FIG. 8 shows a flowchart of a program used to operate the system. The computer 20 initially computes the location of the end effector 32 with the input provided by the sensors 46–55. When the surgeon presses on one of the foot switches, the pedal provides a input signal to the computer. For example, the surgeon may want a closer look at an object in front of the endoscope. The surgeon then presses the top of the first foot switch, depressing the first transducer and providing an input signal to the computer. The input signal is converted into an 12 bit binary string which is received by the processor. The 12 bit string corresponds to a predetermined increment of Δz". The computer is constantly sampling the foot pedal, wherein each sample corresponds to a predetermined increment in the corresponding axis". If the surgeon holds down the foot pedal during two sampling periods then the increment to be moved is 2×Δz". The converter also provides a multiplication factor for each increase in voltage level received from the amplifier of the transducer, so that the increments are increased for each increase in voltage. Thus the surgeon can increase the amount of incremental movement by increasing the pressure on the foot switch.

The processor 78 then determines the new coordinates in the third coordinate system. The incremental movements in the third coordinate system (Δx", Δy" and Δz") are used to compute the increment movements in the second coordinate system (Δz', Δy' and Δz') and the coordinates in the first coordinate system (Δx, Δy' and Δz'). The incremental movements are then used to determine the change in the angles a2, a3 and a4, and the linear movement of actuator 24. The computer provides output signals to the appropriate electric motors to move the robotic arm assembly to the new position. The new Π angle is computed and the process is repeated. The present invention thus allows the surgeon to remotely move a surgical instrument in a manner that directly correlates with the viewing image seen through the endoscope.

In the preferred embodiment, the system moves the end effector 32 so that the endoscope is always aligned in the same orientation relative to the patient. This is accomplished by moving the end effector so that the angle a6 is always equal to zero. Thus after each independent movement of the endoscope, the angle a6 is sensed by the sensor 55. If the angle a6 is not equal to zero, the processor moves the end effector in accordance with the following subroutine.

If a6>zero then the end effector is moved an increment equal to:

$$\Delta \pi = \pi + \text{constant}$$

If a6<zero then the end effector is moved an increment equal to:

$$\Delta \pi = \pi - \text{constant}$$

where;
- Δπ=the incremental angular movement of the end effector.
- π=the preceding angle
- constant=some predetermined incremental angular movement of the end effector.

The processor moves the end effector in accordance with the above described subroutine until the angle a6 is equal to zero. The new π angle is then stored and used for further computation. Maintaining the angle a6 at zero insures that the view seen by the surgeon is in the same orientation for all end effector positions.

Figure 10:
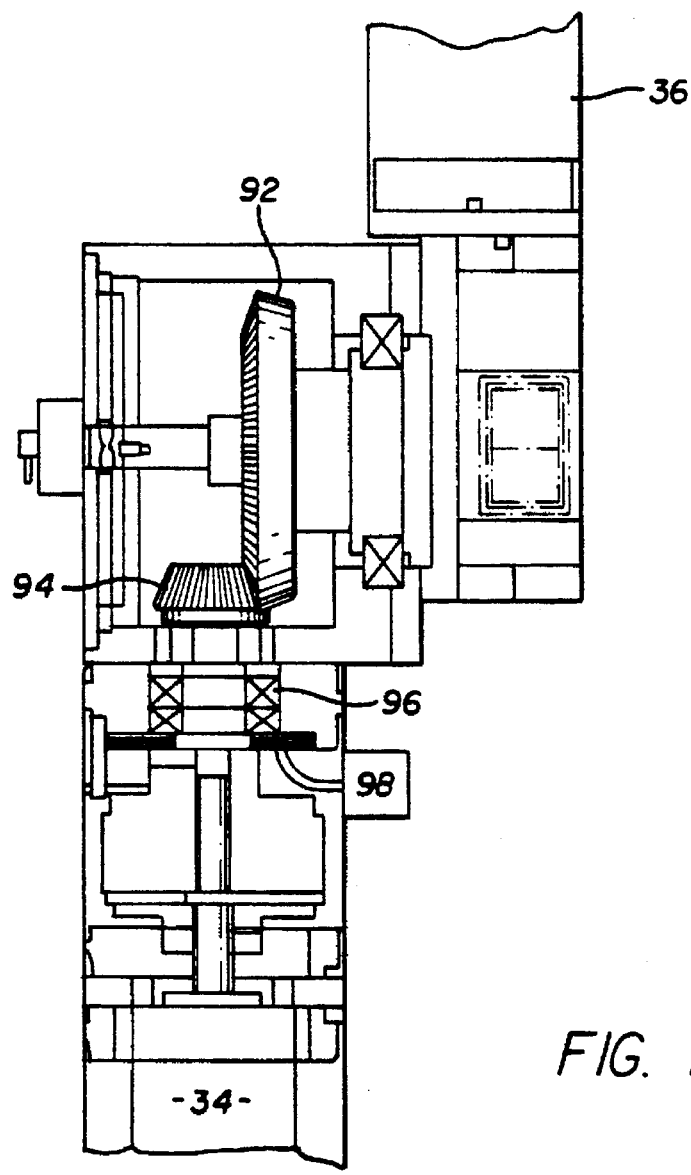
FIG. 10 is a cross-sectional view of the robotic arm assembly showing actuators coupled to clutch and drive train assemblies.

As shown in FIG. 10 each linkage arm 28, 36 or 40 is preferably coupled to a first helical gear 92. The first helical gear 92 is mated with a second helical gear 94 that is coupled to an actuator 30, 34 or 38 by a clutch 96. The clutches 96 are preferably constructed from magnetic plates that are coupled together when power is supplied to the clutches. When power is terminated, the clutches 96 are disengaged and the actuators are decoupled from the drive shafts such that the linkage arms can be manually moved by the operator. Power is supplied to the clutches 96 through a switch 98 which can be operated by the surgeon. The clutches allow the surgeon to disengage the actuators and manually move the position of the endoscope.

As shown in FIG. 6, the system may have a lever actuated input device 100 that is commonly referred to as a "joystick". The input device 100 can be used in the same manner as the foot pedal, wherein the operator can move the endoscope by moving the lever 102 of the device 100. The device 100 may also have a plurality of memory buttons 104 that can be manipulated by the operator. The memory buttons 104 are coupled to the processor of the computer. The memory buttons 104 include save buttons 106 and recall buttons 108. When the save button 106 is depressed, the coordinates of the end effector in the first coordinate system are saved in a dedicated address(es) of the computer memory. When a recall button 108 is pushed, the processor retrieves the data stored in memory and moves the end effector to the coordinates of the effector when the save button was pushed.

The save memory buttons allow the operator to store the coordinates of the end effector in a first position, move the end effector to a second position and then return to the first position with the push of a button. By way of example, the surgeon may take a wide eye view of the patient from a predetermined location and store the coordinates of that location in memory. Subsequently, the surgeon may manipulate the endoscope to enter cavities, etc. which provide a more narrow view. The surgeon can rapidly move back to the wide eye view by merely depressing the recall button of the system. Additionally, the last position of the endoscope before the depression of the recall button can be stored so that the surgeon can again return to this position.

Figure 9:
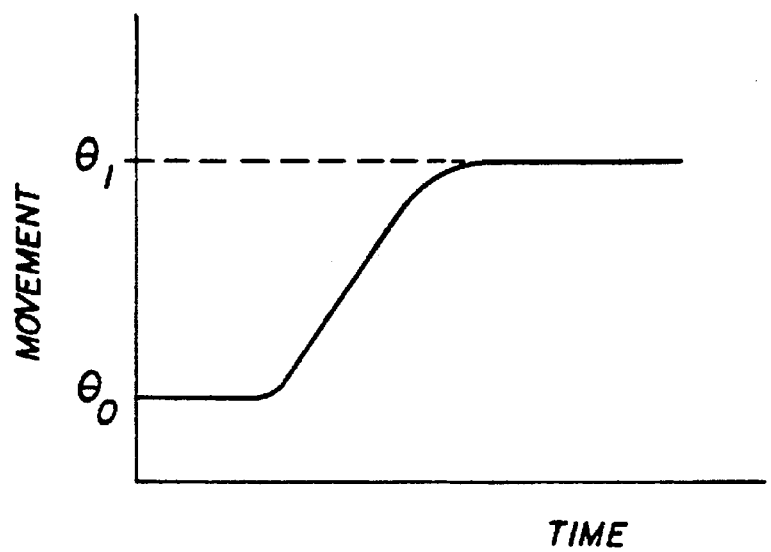
FIG. 9 is a graph showing the incremental movement of the robotic arm assembly.

As shown in FIG. 9, the system is preferably moved during the recall cycle in a ramping fashion so that there is not any sudden movement of the linkage arm assembly. Instead of a purely linear movement of the actuators to move the end effector from point A to point B, the processor would preferably move the linkage arm assembly in accordance with the following equation.

$$\theta(t) = (1-t)^2(\theta_0 + (2\theta_0 + \dot{\theta}_0)t) + t^2(\theta_1 + (2\theta_1 + \dot{\theta}_1)(1-t))$$

where;

t=time $\theta_o$=the initial position of the end effector.

$\theta_1$=the final position of the end effector.

$\dot{\theta}_0$=the velocity of the end effector at position $\theta_o$.

$\dot{\theta}_1$=the velocity of the end effector at position $\theta_1$

By moving each actuator in accordance with the above described algorithm, the linkage arm assembly movement will gradually increase and then gradually decrease as the arm leaves and approaches the original and final positions, respectively. Moving the arm in accordance with the above described equation produces low initial and final arm acceleration values. The gradually increasing and decreasing movement of the arm prevents any abrupt or sudden movement of the arm assembly.

Figure 11:
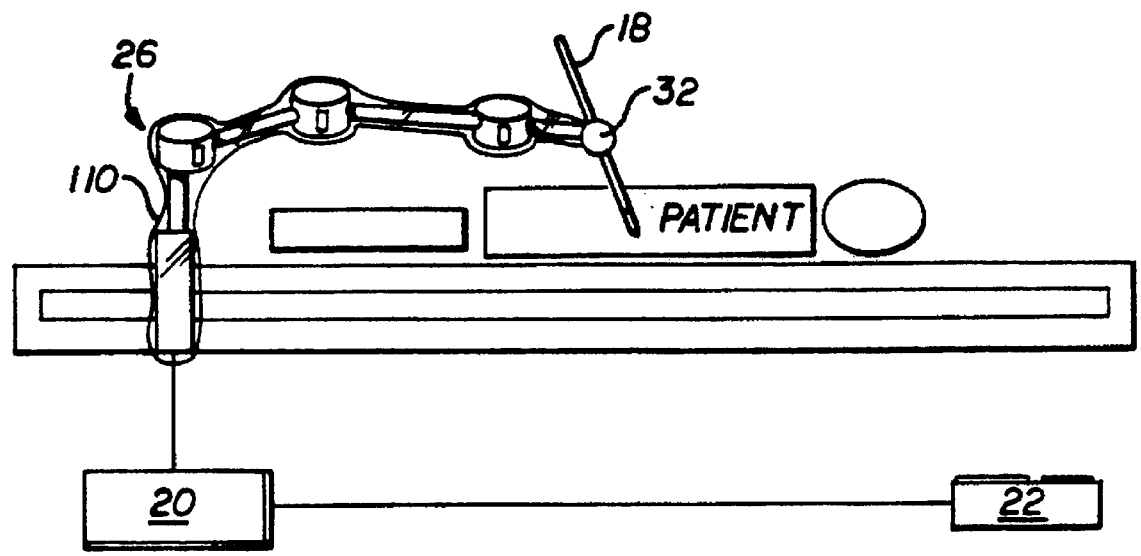
FIG. 11 is a side view of the system showing a protective sterile bag which encapsulates the robotic arm assembly.

As shown in FIG. 11, the robotic arm assembly is preferably encapsulated by a bag 110. The bag 110 isolates the arm assembly 26 so that the arm does not contaminate the sterile field of the operating room. The bag 110 can be constructed from any material suitable to maintain the sterility of the room. The bag 110 may have fastening means such as a hook and loop material or a zipper which allows the bag to be periodically removed and replaced after each operating procedure.

As shown in FIG. 11a, the assembly may have a hand held control device 112 which has buttons 114 that allow the surgeon to control the movement of the end effector in the same manner as the foot pedal described and shown in FIGS. 4 and 5. The control device 112 is also encapsulated by a protective bag 116. The bag 116 is preferably constructed from a material which is both transparent and flexible enough to allow the surgeon to depress the buttons 114. In the preferred embodiment, the bag 116 is constructed from a 0.002 inch polyethylene. The protective bag 116 may have various fastening means to allow the bag 116 to be removed and replaced after each surgical procedure. The application of the bags 110 and 116 allow the assembly to be reused without any scrubbing or sterilization of the equipment.

Figure 12:
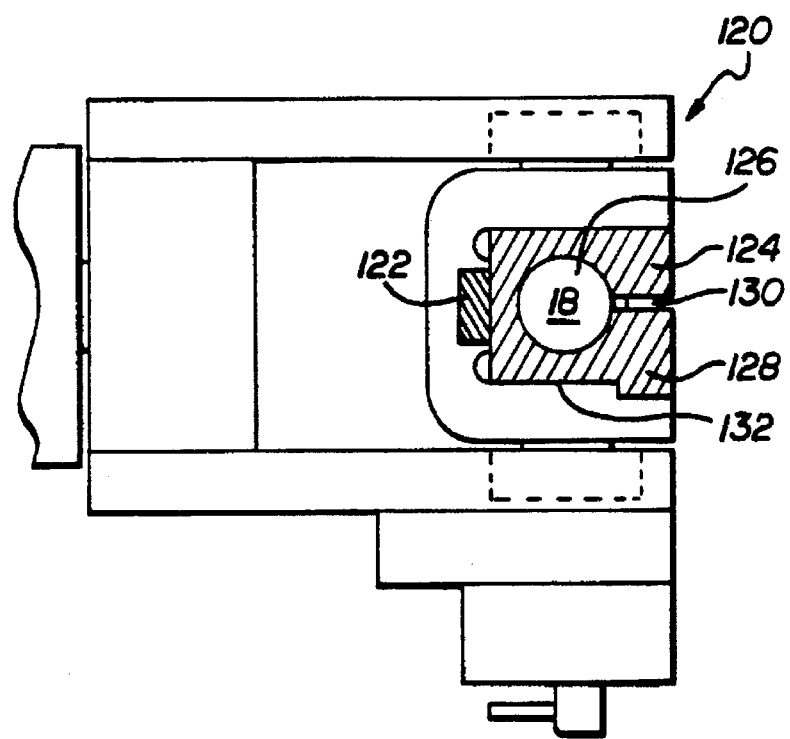
FIG. 12 is a cross-sectional view of an alternate embodiment of the end effector.

FIG. 12 shows an alternate embodiment of an end effector 120. The end effector 120 has a magnet 122 which holds a metal collar 124 that is coupled to the endoscope 18. The collar 124 has a center aperture 126 which receives the endoscope 18 and a pair of arms 128 which together with screw 130 capture the scope 18. The collar 124 is constructed to fit within a channel 132 located in the end effector 120. The magnet 122 is typically strong enough to hold the endoscope during movement of the linkage arm, yet weak enough to allow the operator to pull the collar and scope away from the end effector.

Figure 13:
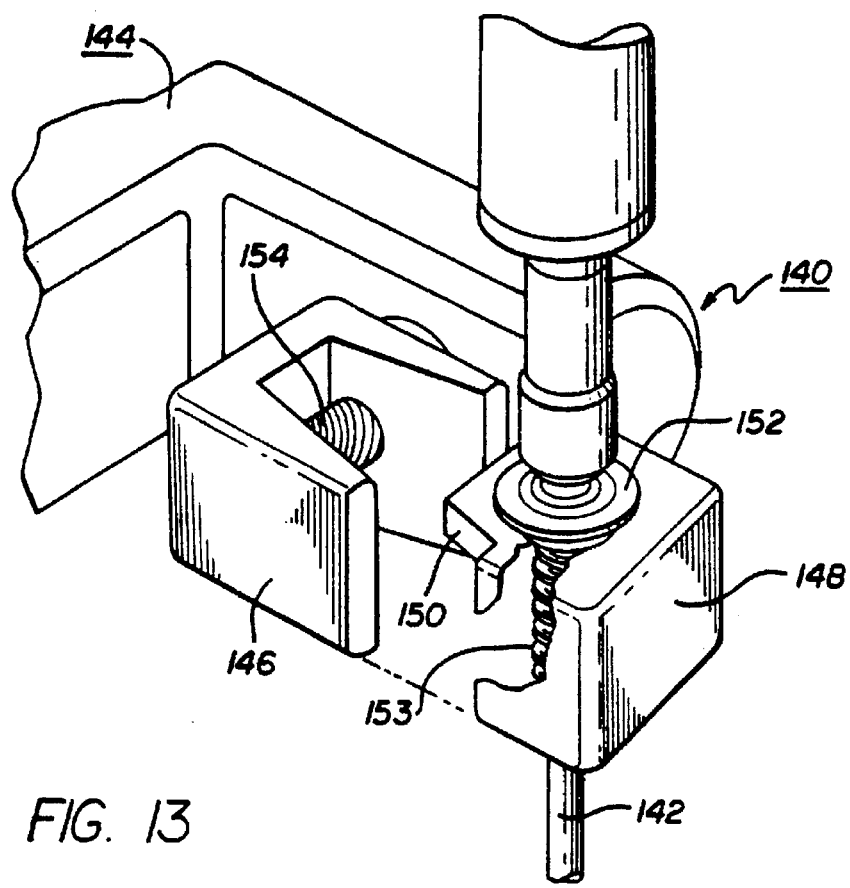
FIG. 13 is a perspective view of an alternate embodiment of an end effector which has a worm gear that is operatively coupled to the surgical instrument.

FIG. 13 shows a preferred embodiment of an end effector 140 that couples the surgical instrument 142 to a robotic system 144. The end effector 140 has a collar holder 146 which can capture a collar 148 that is attached to the instrument 142. The collar 148 has a lip 150 which is supported by the base of the collar holder 146 when the instrument 142 is coupled to the robotic assembly 144. The collar 148 has a bearing 152 that is fastened to the instrument 142 and which has gear teeth 153 that mesh with a worm gear 154 incorporated into the end effector 140. The worm gear 154 is typically connected to an electric motor (not shown) which can rotate the gear 154 and spin the instrument 142 about its longitudinal axis.

Figure 14:
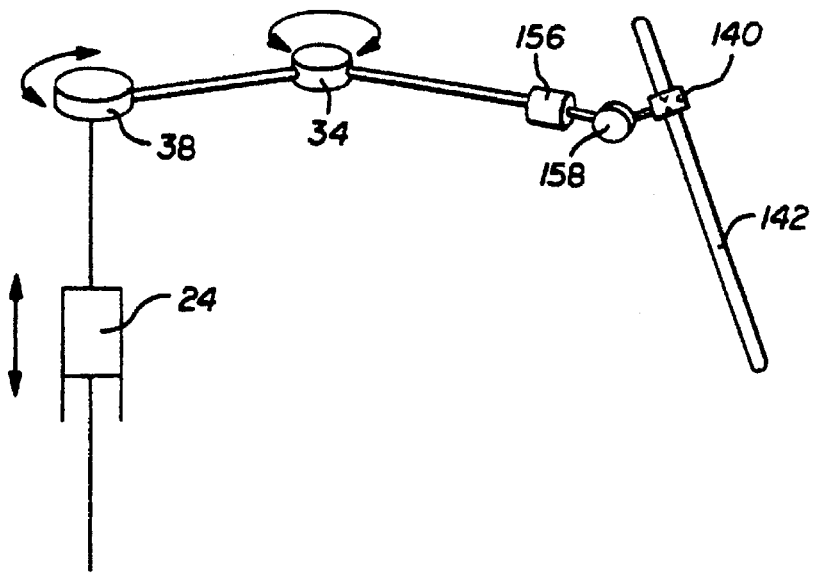
FIG. 14 is a perspective view of an alternate embodiment of a robotic system which incorporates the worm gear joint of FIG. 13.

The end effector 140 is preferably utilized in a robotic system schematically shown in FIG. 14. The worm gear replaces the first actuator 30 of the robotic system shown in FIG. 1. The passive joints 156 and 158 allow the same degrees of freedom provided by the passive joints depicted in FIG. 3. The joints 156 and 158 are shown separately for purposes of clarity, it being understood that the joints may be physically located within the end effector 140.

The surgical instrument is typically coupled to a camera (not shown) and a viewing screen (not shown) such that any spinning of the instrument about its own longitudinal axis will result in a corresponding rotation of the image on the viewing screen. Rotation of the instrument and viewing image may disorient the viewer. It is therefore desirable to maintain the orientation of the viewing image.

In the embodiment shown in FIG. 1, the robotic assembly moves the instrument in accordance with a set of algorithms that maintain the angle a6 at a value of zero. This is accomplished by computing a new angle a6 after each movement and then moving the instrument so that a6 is equal to zero. Depending upon the location of the end effector, moving the instrument to zero a6 may require energizing some or all of the actuators, thus necessitating the computation of the angles a2, a3 and a4. Using the worm gear 154 of the end effector 140, the proper orientation of the viewing image can be maintained by merely rotating the worm gear 154 and scope 142 a calculated angle about the longitudinal axis of the instrument 142.

Figure 15:
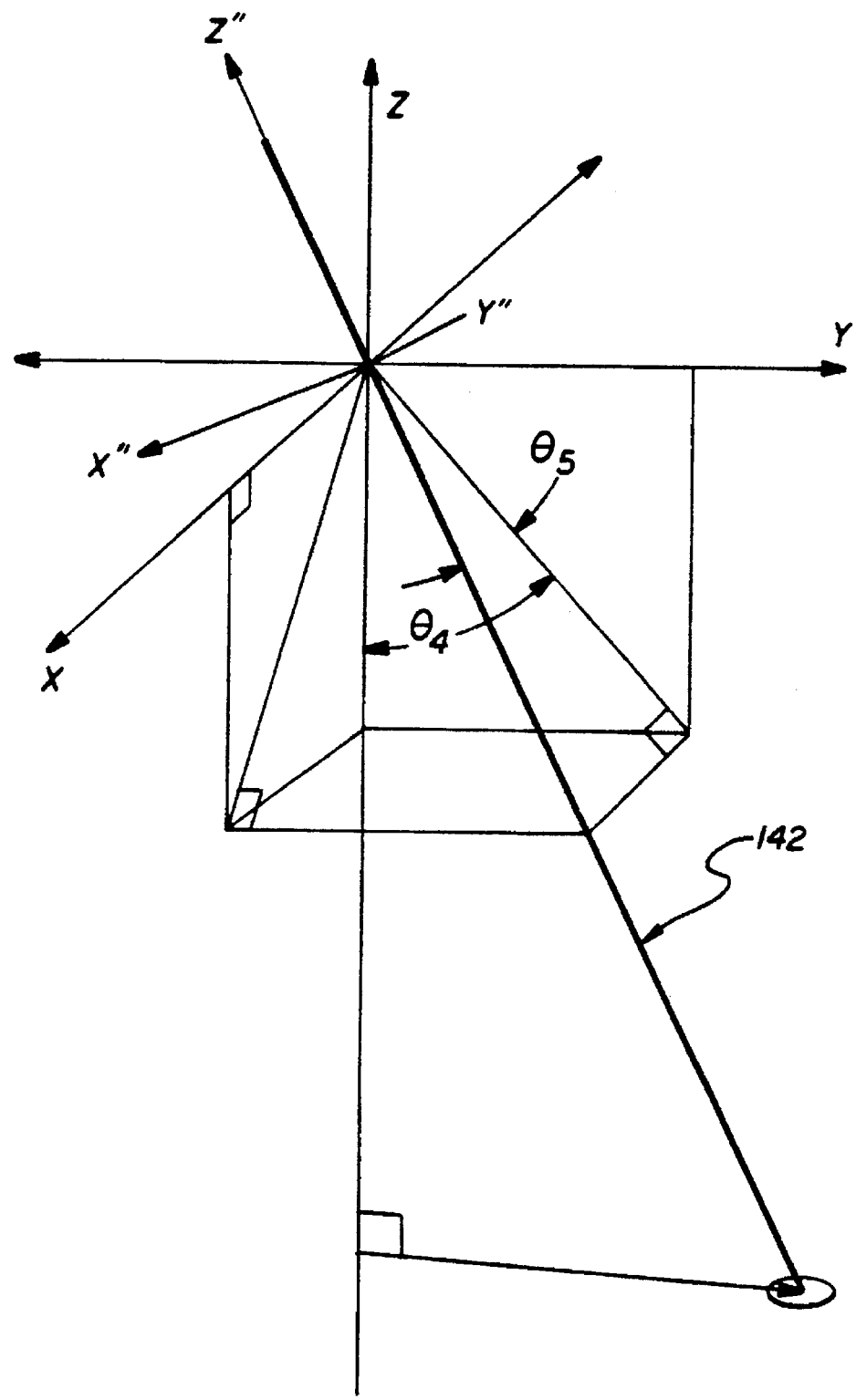
FIG. 15 is a schematic of a surgical instrument that defines a third coordinate system located within a fourth fixed coordinate system.

As shown in FIG. 15, the endoscope 142 is oriented within a fixed fourth coordinate system that has a z axis that is parallel with the z axis of the first coordinate system shown in FIG. 1. The origin of the fourth coordinate system is the intersection of the instrument and the end effector. For purposes of providing reference points, the instrument is initially in a first position and moved to a second position. The endoscope 142 itself defines the third coordinate system, wherein the z" axis coincides with the longitudinal axis of the instrument 142. To insure proper orientation of the endoscope 142, the worm gear 154 rotates the instrument 142 about its longitudinal axis an amount $\Delta\theta 6$ to insure that the y" axis is oriented in the most vertical direction within the fixed coordinate system. $\Delta\theta b$ is computed from the following cross-products.

$$\Delta\theta 6 = zi'' \times (yo'' \times yi'')$$

where;

$\Delta\theta 6$=the angle that the instrument is to be rotated about the z" axis.

yo"=is the vector orientation of the y" axis when the instrument is in the first position.

yi"=is the vector orientation of the y" axis when the instrument is in the second position.

zi"=is the vector orientation of the z" axis when the instrument is in the second position.

The vectors of the yi" and zi" axis are computed with the following algorithms.

$$[zi''] = \begin{bmatrix} \cos\Theta_5 & 0 & -\sin\Theta_5 \\ -\sin\Theta_4\sin\Theta_5 & \cos\Theta_4 & -\sin\Theta_4\cos\Theta_5 \\ \cos\Theta_4\sin\Theta_5 & \sin\Theta_4 & \cos\Theta_4\cos\Theta_5 \end{bmatrix} \begin{bmatrix} 0 \\ 0 \\ 1 \end{bmatrix}$$

$$xi'' = z \times zi''$$
$$yi'' = zi'' \times xi''$$

where;

$\Theta 4$=is the angle between the instrument and the z axis in the y-z plane.

$\Theta 5$=is the angle between the instrument and the z axis in the x-z plane.

z=is the unit vector of the z axis in the first coordinate system.

The angles $\Theta 4$ and $\Theta 5$ are provided by the joint position sensors coupled to the joints 156 and 158. The vector yo" is computed using the angles $\Theta 4$ and $\Theta 5$ of the instrument in the original or first position. For the computation of yi" the angles $\Theta 4$ and $\Theta 5$ of the second position are used in the transformation matrix. After each arm movement yo" is set to yi" and a new yi" vector and corresponding $\Delta\Theta 6$ angle are computed and used to re-orient the endoscope. Using the above described algorithms, the worm gear continuously rotates the instrument about its longitudinal axis to insure that the pivotal movement of the endoscope does not cause a corresponding rotation of the viewing image.

When the surgical instrument is initially inserted into the patient the exact location of the pivot point of the instrument is unknown. It is desirable to compute the pivot point to determine the amount of robotic movement required to move the lens portion of the scope. Accurate movement of the end effector and the opposite lens portion of the instrument can be provided by knowing the pivot point and the distance between the pivot point and the end effector. The pivot point location can also be used to insure that the base of the instrument is not pushed into the patient, and to prevent the instrument from being pulled out of the patient.

The pivot point of the instrument is calculated by initially determining the original position of the intersection of the end effector and the instrument PO, and the unit vector Uo which has the same orientation as the instrument. The position P(x, y, z) values can be derived from the various position sensors of the robotic assembly described above. The unit vector Uo is computed by the transformation matrix:

$$Uo = \begin{bmatrix} \cos\Theta_5 & 0 & -\sin\Theta_5 \\ -\sin\Theta_4\sin\Theta_5 & \cos\Theta_4 & -\sin\Theta_4\cos\Theta_5\Theta_5 \\ \cos\Theta_4\sin\Theta_5 & \sin\Theta_4 & \cos\Theta_4 \end{bmatrix} \begin{bmatrix} 0 \\ 0 \\ -1 \end{bmatrix}$$

After each movement of the end effector an angular movement of the instrument $\Delta\theta$ is computed by taking the arcsin of the cross-product of the first and second unit vectors Uo and U1 of the instrument in accordance with the following line equations Lo and L1.

$$\Delta\theta = \arcsin(|T|)$$
$$T = Uo \times U1$$

where;

T=a vector which is a cross-product of unit vectors Uo and U1.

The unit vector of the new instrument position U1 is again determined using the positions sensors and the transformation matrix described above. If the angle $\Delta\theta$ is greater than a threshold value, then a new pivot point is calculated and Uo is set to U1. As shown in FIG. 16, the first and second instrument orientations can be defined by the line equations Lo and L1:

Lo:

$$xo = Mxo \cdot Zo + Cxo$$
$$yo = Myo \cdot Zo + Cyo$$

L1:

$$x1 = Mx1 \cdot Z1 + Cx1$$
$$y1 = My1 \cdot Z1 + Cy1$$

where;

Zo=a Z coordinate along the line Lo relative to the z axis of the first coordinate system.

Z1=a Z coordinate along the line L1 relative to the z axis of the first coordinate system.

Mxo=a slope of the line Lo as a function of Zo.

Myo=a slope of the line Lo as a function of Zo.

Mx1=a slope of the line L1 as a function of Z1.

My1=a slope of the line L1 as a function of Z1.

Cxo=a constant which represents the intersection of the line Lo and the x axis of the first coordinate system.

Cyo=a constant which represents the intersection of the line Lo and the y axis of the first coordinate system.

Cx1=a constant which represents the intersection of the L1 and the x axis of the first coordinate system.

Cy1=a constant which represents the intersection of the line L1 and the y axis of the first coordinate system.

The slopes are computed using the following algorithms:

$$Mxo = Uxo/Uzo$$
$$Myo = Uyo/Uzo$$
$$Mx1 = Ux1/Uz1$$
$$My1 = Uy1/Uz1$$
$$Cx0 = Pox - Mx1 \cdot Poz$$
$$Cy0 = Poy - My1 \cdot Poz$$
$$Cx1 = Plx - Mx1 \cdot Plz$$
$$Cy1 = Ply - My1 \cdot Plz$$

where;

Uo(x, y and z)=the unit vectors of the instrument in the first position within the first coordinate system.

U1(x, y and z)=the unit vectors of the instrument in the second position within the first coordinate system.

Po(x, y and z)=the coordinates of the intersection of the end effector and the instrument in the first position within the first coordinate system.

P1(x, y and z)=the coordinates of the intersection of the end effector and the instrument in the second position within the first coordinate system.

To find an approximate pivot point location, the pivot points of the instrument in the first orientation Lo (pivot point Ro) and in the second orientation L1 (pivot point R1) are determined, and the distance half way between the two points Ro and R1 is computed and stored as the pivot point Rave of the instrument. The pivot point $R_{ave}$ is determined by using the cross-product vector T.

To find the points Ro and R1 the following equalities are set to define a line with the same orientation as the vector T that passes through both Lo and L1.

$$tx=Tx/Tz$$

$$ty=Ty/Tz$$

where;

tx=the slope of a line defined by vector T relative to the Z-x plane of the first coordinate system.

ty=the slope of a line defined by vector T relative to the Z-y plane of the first coordinate system.

Tx=the x component of the vector T.

Ty=the y component of the vector T.

Tz=the z component of the vector T.

Picking two points to determine the slopes Tx, Ty and Tz (eg. Tx=x1−xo, Ty=y1−yo and Tz=z1−z0) and substituting the line equations Lo and L1, provides a solution for the point coordinates for Ro (xo, yo, zo) and R1 (x1, y1, z1) as follows.

$$zo=((Mx1-tx)z1+Cx1-Cxo)/(Mxo-tx)$$

$$z1=((Cy1-Cyo)(Mxo-tx)-(Cx1-Cxo)(Myo-ty))/((Myo-ty)(Mxo-tx))$$

$$yo=Myo \cdot zo+Cyo$$

$$y1=My1 \cdot z1+Cy1$$

$$xo=Mxo \cdot zo+Cxo$$

$$x1=Mx1 \cdot z1+Cx1$$

The average distance between the pivot points Ro and R1 is computed with the following equation and stored as the pivot point of the instrument.

$$R_{ave}=((x1+xo)/2, (y1+yo)/2, (z1+zo)/2)$$

The pivot point can be continually updated with the above described algorithm routine. Any movement of the pivot point can be compared to a threshold value and a warning signal can be issued or the robotic system can become disengaged if the pivot point moves beyond a set limit. The comparison with a set limit may be useful in determining whether the patient is being moved, or the instrument is being manipulated outside of the patient, situations which may result in injury to the patient or the occupants of the operating room.

FIGS. 17 and 18 show the linear actuator 24 of the robotic arm assembly 16 coupled to a cart 200. The cart 200 may have shelves (not shown) which store the computer of the system. The cart 200 has wheels 202 that allow the operator to move the assembly to and from an operating table 204. The robotic assembly 16 is attached to the operating table 204 by a mounting assembly 206. The mounting assembly 206 includes a mounting plate 208 which has a pair of L shaped rigid clamp portions 210 and a pair of pivot clamps 212 that are pivotally connected to the plate 208. Conventional operating tables 204 have hand rails 214 that extend from the sides of the bed 204. The clamps 212 are adapted to grasp the hand rails 214 and mount the robotic assembly 206 to the table 204.

FIGS. 19–23 show a preferred embodiment of the mounting assembly 206. Each pivot clamp 212 is coupled to the mounting plate 208 by a pivot pin 216. The pivot clamps 212 are biased into a closed position by a clamp spring 218 that is secured at each end by spring pins 220 which extend into the mounting plate 208.

Figure 23:
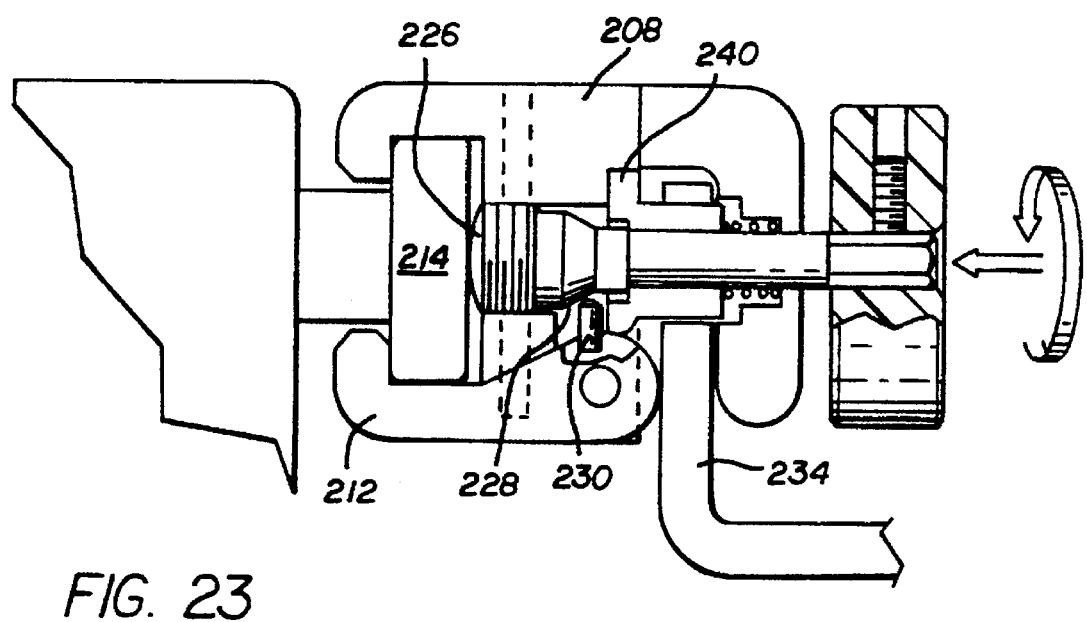
FIG. 23 is a side view showing the clamping mechanism in a closed position.
Figure 28:
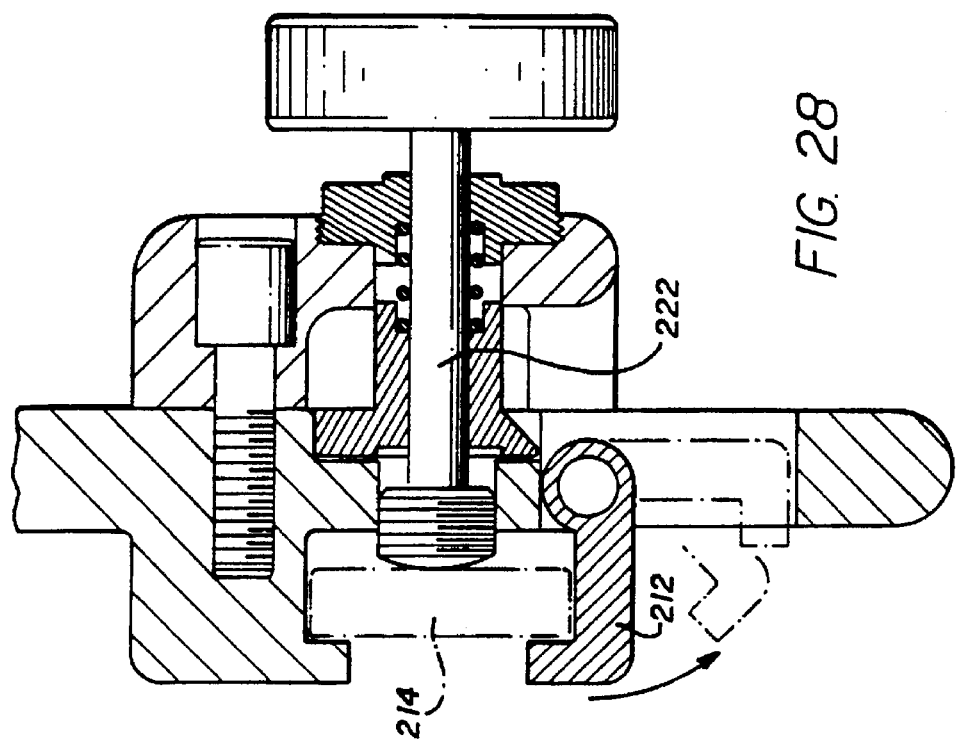
FIG. 28 is a cross-sectional view taken at line 28—28 of FIG. 27.
Figure 27:
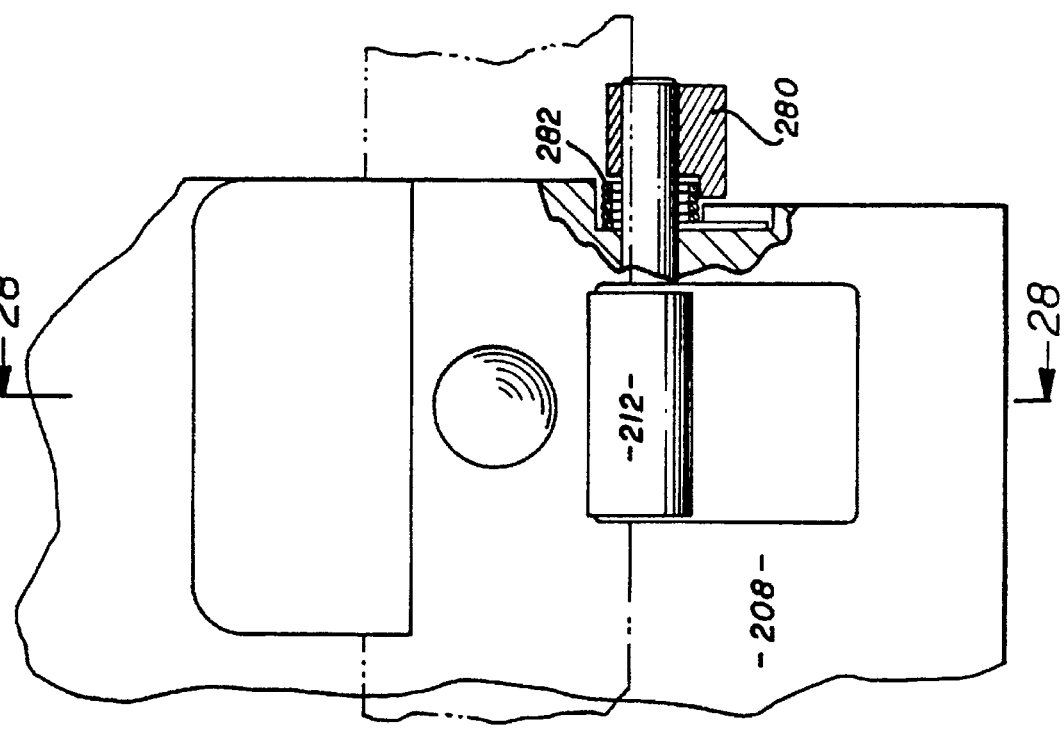
FIG. 27 is a front view of the alternate clamping mechanism.

The mounting assembly 206 has screws 222 which extend through the mounting plate 208. At one end of each screw 222 is a knob 224 that allows the operator to rotate the screw 222. At the opposite end of each screw 222 is a threaded head 226 which cooperates with a threaded aperture 227 within the plate 208. The mounting plate 208 has a back plate 260 attached to a front plate 262 by a dowel pin 264 and a screw 266. As shown in FIG. 23, the end of the head 226 engages and applies a pressure to the hand rail 214 to further secure the robotic assembly 16 to the table 204.

Figure 22:
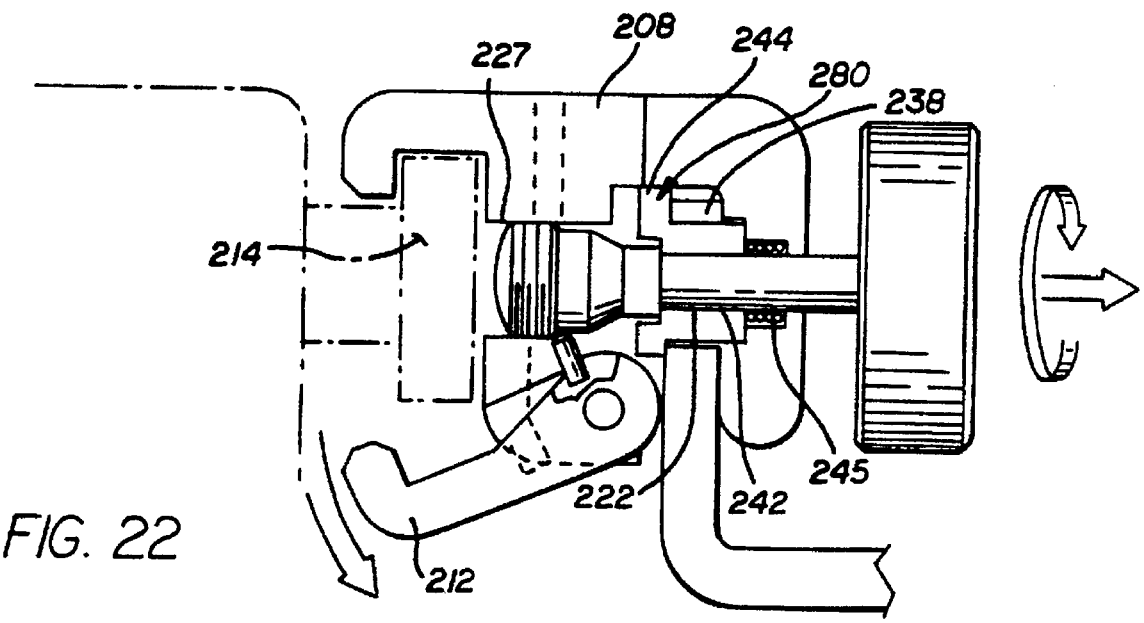
FIG. 22 is a side view showing the clamping mechanism in an open position.

Each screw 222 has a cam surface 228 which engages a pin 230 located within the mounting plate 208. The pin 230 also engages the pivot clamp 212. When the screw 222 is moved away from the hand rail 214, the cam surface 228 pushes the pin 230 in a downward direction as shown in FIG. 22. The downward movement of the pin 230 rotates the pivot clamp 212 in a counterclockwise direction away from the hand rail 214, disengaging the mounting assembly 206 from the table 204. When the screw 222 is screwed back toward the hand rail 214, the spring 218 rotates the clamp 212 back into engagement with the rail 214. The movement of the screw 222, moves the cam surface 228 and allows the pin 230 to move in an upward direction.

Referring to FIG. 17, the cart 200 has a pair of flange plates 234 located at each side of the linear actuator 24. Each flange plate 234 has a pair of ears 236 separated by a slot 238. As shown in FIG. 22, the clamping mechanism 206 has a cart clamp 240. The cart clamp 240 has a bore 242 that allows the screw 222 to extend therethrough. The cart clamp 240 also has a shoulder 244 with an outer diameter larger than the width of the flange slot 238. Moving the screws away from the hand rail 214 presses the cart clamps 240 into the flange plates 234 and secures the mounting plate 208 and robotic assembly 16 to the cart 200. When the screws 222 are screwed toward the hand rail 214, the cart clamps 240 are released from the flange plates 238 and the mounting plate 208 is allowed to move relative to the cart 200. The clamping mechanism 206 may include a spring 245 that biases the clamp 240 away from the flange 234. Detaching the mounting plate 208 from the cart 220 when the pivot clamp 212 is grasping the hand rail 214, allows the plate 208 to float and compensating for any lack of colinearity between the table 204 and the cart 200.

FIGS. 20 and 21 show the linear actuator 24 coupled to the mounting plate 208. The assembly includes a screw 246 that has a threaded shaft 247 which extends through an arcuate shaped slot 248 in the mounting plate 208 and screws into a threaded aperture 249 in the linear actuator 24. The mount screw 246 that may have a shoulder 250 or a washer (not shown) which is pressed against the mounting plate 208. The actuator 24 is attached to the mounting plate 208 by a wavy spring 252 that is captured by a lid 254 and a plurality of screws 256 that are inserted in on opening 258 of the mounting plate 208. The operator can rotate the robotic assembly 16 relative to the operating table by unscrewing the screw 246 and moving the actuator 24 and threaded shaft 247 along the arcuate shaped slot 248 of the mounting plate 208. Rotation of the robotic assembly allows the operator to move and properly align the arm of the system.

In operation, the cart 200 is wheeled up to the table 204 such that the top L shaped clamp portions 210 of the mounting assembly 206 grab the hand rail 214. As shown in FIG. 23, the screws 222 are screwed further into the mounting plate 208 to allow the springs 218 to pull the pivot clamps 212 into engagement with the hand rail 214. The movement of the screw 222 also releases the mounting plate 208 from the cart 200. The orientation of the robotic assembly 16 can be varied by unscrewing the mount screw 246 and moving the linear actuator 24 along the arcuate slot of the mounting plate 208, and then tightening the screw 246.

As shown in FIG. 22, after the surgical procedure, the screws 222 can be screwed away from the table 204, so that the pivot clamps 212 rotate away from the hand rail 214 and the cart clamps 240 become secured to the cart 200. The cart 200 can then be wheeled away for future use. The mounting assembly and cart of the present invention provide mobility for the robotic assembly and allow the system to be easily stored and transported to various surgical fields.

FIGS. 24–28 show an alternate embodiment of the clamping mechanism. The mechanism includes a handle 280 that is attached to the clamp pin 216. Rotation of the handle 280 rotates the pivot clamp 212. This embodiment does not use the pin 230, spring 218 and screw cam surface 228 of the embodiment shown in FIGS. 17–23 to move the pivot claims 212. The pin 216 is coupled to a torsion spring 282 that is captured by grooves 284 and 286 in the mounting plate 208 and handle 280, respectively. The torsion spring 282 biases the pivot clamp 212 into engagement with the hand rail 214. The handle 280 has a ball detent screw 288 that is pressed into a detent hold 290 in the mounting plate 208, to maintain the handle 280 in an open position. Alternatively, both the mounting plate 208 and handle 260 may have attractive magnets (not shown) which maintain the pivot clamp 212 in a position away from the hand rail 214. To clamp the mounting plate 208 to the hand rail 214, the operator pushes the handle 280 until the ball detent screw 288 is separated from the mounting plate 208 and the spring 282 snaps the pivot clamp 212 onto the rail 214. The pivot clamp 212 is disengaged by manually rotating the handle 280 to the open position and resetting the ball detent screw 288 into the detent hole 290.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A surgical apparatus that manipulates a surgical instrument, comprising:

an end effector for holding the surgical instrument;

a first linkage arm connected to said end effector;

a first active actuator which has an output shaft that is connected to said first linkage arm, said output shaft is moved by said first active actuator, said movement of said output shaft moves said first linkage arm and said end effector;

a computer for controlling said first active actuator; and a first clutch that decouples said output shaft of said first active actuator from said first linkage arm to allow said end effector to be manually manipulated.

2. The apparatus as recited in claim 1, further comprising a second linkage arm that is connected to said first active actuator and an output shaft of a second active actuator and a second clutch that decouples said second linkage arm from said output shaft of said second active actuator.

3. The apparatus as recited in claim 2, wherein each of said first and second clutches is an electromagnetic device which disengages and allows manual manipulation of said end effector when power is terminated to said clutches.

4. The apparatus as recited in claim 1, further comprising a button that can be depressed to decouple said first active actuator from said end effector.

5. The apparatus as recited in claim 1, wherein said first active actuator is an electric motor.

6. The apparatus as recited in claim 1, further comprising an input device that is coupled to said computer, said input device for receiving command signals from a user.

7. The apparatus as recited in claim 1, further comprising a pair of passive joints that are coupled to said first linkage arm and said end effector.

* * * * *